United States Patent
Shemonski et al.

(10) Patent No.: US 10,719,932 B2
(45) Date of Patent: Jul. 21, 2020

(54) IDENTIFYING SUSPICIOUS AREAS IN OPHTHALMIC DATA

(71) Applicant: Carl Zeiss Meditec, Inc., Dublin, CA (US)

(72) Inventors: Nathan D. Shemonski, San Francisco, CA (US); Mary K. Durbin, San Francisco, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 96 days.

(21) Appl. No.: 15/909,658

(22) Filed: Mar. 1, 2018

(65) Prior Publication Data
US 2019/0272631 A1 Sep. 5, 2019

(51) Int. Cl.
*G06K 9/00* (2006.01)
*G06T 7/00* (2017.01)
(Continued)

(52) U.S. Cl.
CPC .......... *G06T 7/0012* (2013.01); *A61B 3/0025* (2013.01); *A61B 3/102* (2013.01);
(Continued)

(58) Field of Classification Search
CPC ......... G06T 5/003; G06T 7/0012; G06T 7/11; G06T 7/143; G06T 7/0014; G06T 7/40; G06T 7/41; G06T 2207/30041; G06T 2207/20076; G06T 2207/10101; G06T 2207/30101; G06T 2207/10012; G06T 2207/20081; G06T 2207/20096; G06T 2207/30104; G06T 2207/20084; G06T 2207/30024; G06T 2207/10148;
(Continued)

(56) References Cited

U.S. PATENT DOCUMENTS 5,868,134 A * 2/1999 Sugiyama ............ G06T 7/0012
600/300
7,712,898 B2 5/2010 Abramoff et al.
(Continued)

FOREIGN PATENT DOCUMENTS

| WO | 2014/097164 A1 | 6/2014 |
| WO | 2016/139183 A1 | 9/2016 |
| WO | 2016/177722 A1 | 11/2016 |

OTHER PUBLICATIONS

Bogunović et al., "Personalized Prognosis in Early/Intermediate Age-Related Macular Degeneration based on Drusen Regression", Optima, Arvo, 2017, 1 page.
(Continued)

*Primary Examiner* — Jose L Couso
(74) *Attorney, Agent, or Firm* — Morrison & Foerster LLP

(57) ABSTRACT

An ophthalmic image diagnostic tool and method submits a test image to a neural network trained to identify abnormal regions of an ophthalmic image, to distinguish between multiple types of abnormalities, and to associate an abnormality type with each identified potentially abnormal region. Each potentially abnormal region in the test image is highlighted, and in response to a user-selection of a highlighted region, a previously diagnosed sample (e.g., from a library of samples) of the abnormality type associated with the selected highlighted region is displayed.

21 Claims, 7 Drawing Sheets

(51) Int. Cl.
  *A61B 3/00* (2006.01)
  *A61B 3/10* (2006.01)
(52) U.S. Cl.
  CPC .............. *G06T 2207/10101* (2013.01); *G06T 2207/30041* (2013.01)
(58) Field of Classification Search
  CPC ....... G06T 2207/10152; G06T 2210/41; A61B 3/0025; A61B 3/102; A61B 3/14; A61B 3/12; A61B 3/10; A61B 3/152; A61B 3/1233; A61B 3/1241; A61B 3/13; A61B 5/7246; A61B 5/7275; A61B 5/0066; A61B 5/0073; A61B 5/02007; A61B 5/4842; A61B 5/4878; A61B 5/7267; A61B 5/0013; A61B 2576/02; G06K 9/0061; G06K 9/00617; G06K 9/00597; G06K 9/4619; G06K 9/4609; G06K 9/4623; G06K 9/4628; G06K 9/4652; G06K 9/627; G06K 9/6292; G06K 9/00147; G06K 9/6287; G06K 9/6267; G06K 9/628; G06K 9/629; G06K 2009/4666; G06K 2209/05; G06N 3/0454; G06N 3/082; G06N 3/0427; G06N 3/0445; G06N 3/063; G06N 3/084; G06N 3/006; G06N 3/04; G06N 3/08; G06N 5/003; G06N 20/00; G01B 9/02044; G01B 9/02083; G01B 9/02091; G16H 30/40; G16H 50/20; G06F 17/18; G06F 17/5018; G06F 2217/16; A61N 2005/0648
  See application file for complete search history.

(56) References Cited

U.S. PATENT DOCUMENTS

| | | | |
|---|---|---|---|
| 7,945,312 | B2 | 5/2011 | Hular et al. |
| 8,831,304 | B2 | 9/2014 | Xu et al. |
| 8,879,813 | B1* | 11/2014 | Solanki .................. G16H 30/20 382/128 |
| 8,896,682 | B2 | 11/2014 | Bressler et al. |
| 8,971,612 | B2 | 3/2015 | Shotton et al. |
| 9,355,446 | B2* | 5/2016 | Imamura ................ G06T 7/0012 |
| 9,462,945 | B1 | 10/2016 | Barriga et al. |
| 9,775,506 | B2 | 10/2017 | Burlina et al. |
| 10,383,514 | B2* | 8/2019 | Imamura .............. A61B 3/1025 |
| 10,441,163 | B2* | 10/2019 | Miyasa .............. G06K 9/00604 |
| 2004/0054358 | A1* | 3/2004 | Cox .................... A61F 9/00806 606/5 |
| 2005/0288573 | A1 | 12/2005 | Timmins |
| 2010/0290005 | A1* | 11/2010 | Huang .................. A61B 3/102 351/206 |
| 2011/0137157 | A1* | 6/2011 | Imamura ............... G06T 7/0012 600/425 |
| 2011/0170062 | A1* | 7/2011 | Isogai .................... A61B 3/102 351/206 |
| 2012/0127428 | A1* | 5/2012 | Isogai .................... A61B 3/102 351/206 |
| 2012/0130270 | A1* | 5/2012 | Imamura ............... G06T 7/0012 600/558 |
| 2012/0257164 | A1* | 10/2012 | Zee ......................... A61B 3/12 351/206 |
| 2015/0272432 | A1* | 10/2015 | Satake ................. A61B 3/0025 351/206 |
| 2015/0272434 | A1* | 10/2015 | Satake ................. A61B 3/0058 351/206 |
| 2016/0000324 | A1* | 1/2016 | Rege ...................... A61B 3/008 351/206 |
| 2016/0278627 | A1* | 9/2016 | Huang ................. A61B 3/0025 |
| 2016/0284103 | A1* | 9/2016 | Huang ................. G06T 7/0012 |
| 2017/0112377 | A1* | 4/2017 | Shiba ................... A61B 3/1233 |
| 2017/0323446 | A1* | 11/2017 | Iwase .................... A61B 3/102 |
| 2017/0357879 | A1 | 12/2017 | Odaibo et al. |
| 2018/0012359 | A1 | 1/2018 | Prentasic et al. |
| 2018/0153399 | A1* | 6/2018 | Fink ..................... A61B 3/0033 |
| 2019/0082957 | A1* | 3/2019 | Fujii ........................ A61B 3/12 |
| 2019/0110753 | A1* | 4/2019 | Zhang ...................... A61B 3/12 |
| 2019/0191988 | A1* | 6/2019 | Gargeya .................. A61B 3/12 |
| 2019/0220973 | A1* | 7/2019 | Cho ....................... G06T 7/0012 |

OTHER PUBLICATIONS

Herrmann et al., "Content Based Image Retrieval (CBIR) in Remote Clinical Diagnosis and Healthcare", Encyclopedia of E-Health and Telemedicine, Oct. 2016, 28 pages.

Hwang et al., "Automated Quantification of Capillary Nonperfusion Using Optical Coherence Tomography Angiography in Diabetic Retinopathy", Journal of the American Medical Association Ophthalmology, vol. 134, No. 4, Apr. 1, 2016, pp. 367-373.

Kanagasingam et al., "Progress on Retinal Image Analysis for Age Related Macular Degeneration", Progress in Retinal and Eye Research, vol. 38, 2014, pp. 20-42.

Kwon et al., "Alterations of the Foveal Avascular Zone Measured by Optical Coherence Tomography Angiography in Glaucoma Patients With Central Visual Field Defects", Investigative Ophthalmology & Visual Science, vol. 58, No. 3, Mar. 2017, pp. 1637-1645.

Lee et al., "Deep Learning is Effective for Classifying Normal Versus Age-Related Macular Degeneration OCT Images", Ophthalmology Retina, vol. 1, No. 4, Jul.-Aug. 2017, pp. 322-327.

Seeböck et al., "Defining Disease Endophenotypes in Neovascular AMD by Unsupervised Machine Learning of Large-Scale OCT Data", Optima, Arvo, 2017, 1 page.

"TinEye", Wikipedia, Available online at <https://en.wikipedia.org/w/index.php?title=TinEye&oldid=828899381>, Mar. 5, 2018, pp. 1-3.

Venugopal et al., "Repeatability of Vessel Density Measurements of Optical Coherence Tomography Angiography in Normal and Glaucoma Eyes", The British Journal of Ophthalmology, vol. 102, No. 3, Mar. 2018, pp. 1-2 (English Abstract Only).

Yarmohammadi et al., "Optical Coherence Tomography Angiography Vessel Density in Healthy, Glaucoma Suspect, and Glaucoma Eyes", Investigative Ophthalmology & Visual Science, vol. 57, No. 9, 2016, pp. OCT451-OCT459.

Zahid et al., "Fractal Dimensional Analysis of Optical Coherence Tomography Angiography in Eyes With Diabetic Retinopathy", Investigative Ophthalmology & Visual Science, vol. 57, No. 11, Sep. 2016, pp. 4940-4947.

Zhang et al., "A Survey on Computer Aided Diagnosis for Ocular Diseases", BMC Medical Informatics and Decision Making, vol. 14, No. 80, 2014, pp. 1-29.

\* cited by examiner

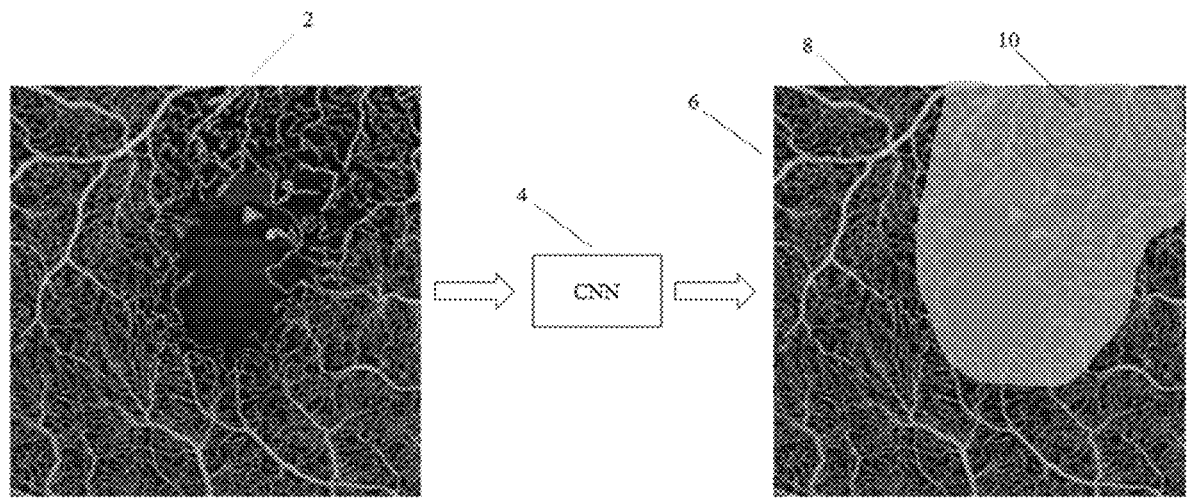
FIG. 6
FIG. 8
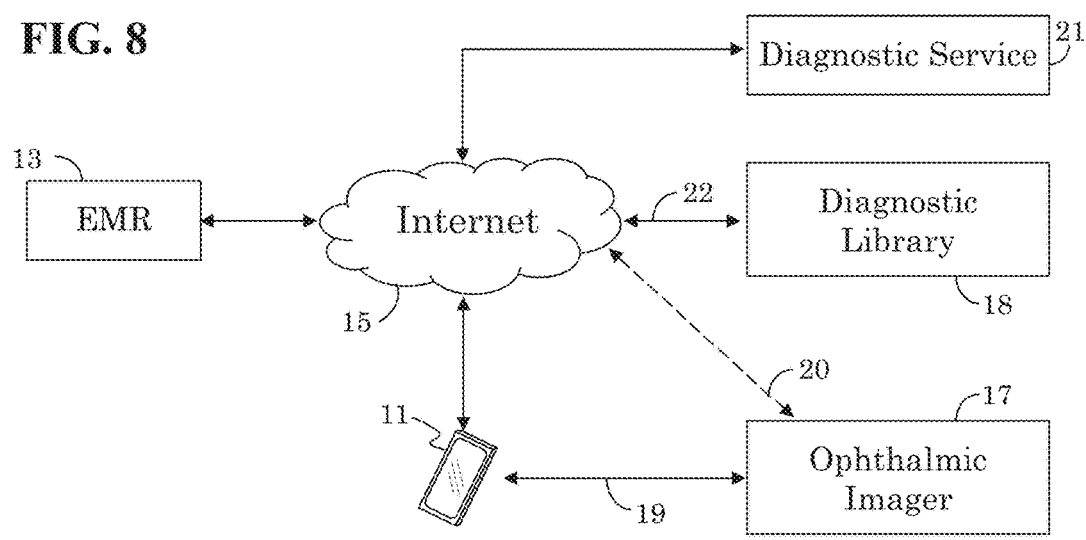

IDENTIFYING SUSPICIOUS AREAS IN OPHTHALMIC DATA

BACKGROUND

Field of Invention

The present invention is generally directed to the field of medical equipment. More specifically, it is directed to ophthalmic medical tools for aiding the reviewing of ophthalmic images for diagnostic purposes.

Description of Related Art

Analyzing ophthalmic images, such as images captured by optical coherence tomography (OCT) typically requires an experienced examiner (e.g., expert) who relies on previous experience to identify suspicious areas of an OCT image. Attempts have been made to assist an examiner in diagnosing a malady from an OCT image.

Previously, specific metrics such as vascular density, foveal avascular zone (FAZ) circularity, fractal dimension, flow voids, regions of non-perfusion, etc. have been used for automated analysis of optical coherence tomography angiography (OCTA) images. These metrics, however, only focus on a single aspect of an OCTA dataset. That is, they may focus on identifying one specific type of ophthalmic pathology.

Previous automated systems to aid in the analyzing of OCT data have also highlighted suspicious regions of an input OCT data image. An expert, however, still needed to uses his/her knowledge of past cases, and remember cases similar to a newly imaged patient to explain the highlighted regions. This is because the automated system may highlight a region as 'not normal' simply for the presence of geographic atrophy (GA) or for being outside normal thickness bounds. Use of more general convolutional neural networks have also been used to analyze OCT cross-sectional data (e.g., B-scan).

It is an object of the present invention to provide a more comprehensive automated analysis system to de-skill the use of an ophthalmic imaging system, such as an OCT system.

It is a further object of the present invention to provide a method, device, or system for automated analysis of OCT Angiography (image) data.

SUMMARY OF INVENTION

The above objects are met in an ophthalmic image diagnostic tool, method, and/or system that uses machine learning (e.g., convolutional neural networks, CNN) to provide an initial diagnosis from an input ophthalmic image, and provides additional tools/mechanisms to help a physician to better analyze the input ophthalmic image. The input ophthalmic image may be any of various types of ophthalmic images, such as a fundus image taken by a fundus imager, an optical coherence tomography (OCT) image taken by an OCT system (e.g. an A-scan, B-scan, or en face image), an angiography image (e.g., OCT angiography or fluorescein angiograph (FA)), etc. The different types of ophthalmic images may each have their advantages in diagnosing (i.e. identifying) different types of ophthalmic maladies (e.g., uveitis, diabetic retinopathy, glaucoma, central retinal artery occlusion, micro-aneurysms, neovascularization, soft or hard exudates, hemorrhages, macular degeneration, retinal vein occlusion, etc.). Therefore, it is preferred that the machine learning mechanism be trained on different types of images, but it may also be trained to diagnose multiple different types of ophthalmic maladies on any one specific type of ophthalmic image. For example, the tool may be trained to analyze OCT angiography images, in particular, and be incorporated into an OCT system or an OCT periphery device. For ease of discussion, it is herein assumed that the machine learning mechanism is implemented as a neural network.

In some embodiments, a test ophthalmic image to be analyzed (e.g. an OCT angiography (OCTA) image) may be submitted to a neural network (e.g. a CNN) trained to identify potentially abnormal regions of an ophthalmic image (such as trained to identify ophthalmic maladies in OCTA images). The neural network may further be trained to distinguish between multiple different types of abnormalities (such as recited above), and to associate at least one specific abnormality type with each identified potentially abnormal region. Any region of the submitted test ophthalmic image that is identified as a potentially abnormal region may be highlighted to define an annotated ophthalmic image. The annotated ophthalmic image may be stored or displayed for review.

If displayed, the highlighted regions may preferably be selectable, and the ophthalmic image diagnostic tool/method/system may respond to a user-selection of a highlighted region by displaying one or more previously diagnosed ophthalmic samples from a so-called 'Atlas' that resemble (or have similar characteristic feature as) the highlighted region or are examples of the specific abnormality type associated with the selected highlighted region. The displayed diagnosed ophthalmic sample(s) may also be extracted from a library of diagnosed ophthalmic samples, and/or may be images from the same patient from which the input ophthalmic image was taken. Viewing images of similar regions from the patient's medical history may be helpful in noting progression, e.g., changes over time, of the specific malady. The library of diagnosed ophthalmic samples may maintain at least one diagnosed ophthalmic sample associated with each of the multiple of abnormality types identifiable by the neural network.

Other objects and attainments together with a fuller understanding of the invention will become apparent and appreciated by referring to the following description and claims taken in conjunction with the accompanying drawings.

The embodiments disclosed herein are only examples, and the scope of this disclosure is not limited to them. Particular embodiments may include all, some, or none of the components, elements, features, functions, operations, or steps of the embodiments disclosed above. Embodiments according to the invention are in particular disclosed in the attached claims, which may be directed to a method, a storage medium, a system, a device and/or a computer program product, and any feature mentioned in one claim category, e.g. method, can be claimed in another claim category, e.g. system, as well. Claim dependencies or references-back to another claim are chosen for formal reasons only. Any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

BRIEF DESCRIPTION OF THE DRAWINGS

In the drawings wherein like reference symbols refer to like parts.

FIG. 6 illustrates an operational flow in accord with the present invention, including a graphical user interface output.

FIG. 8 illustrates an overview of ophthalmic image diagnostic system in accord with some embodiments of the present invention.

DESCRIPTION OF THE PREFERRED EMBODIMENTS

Figure 1:
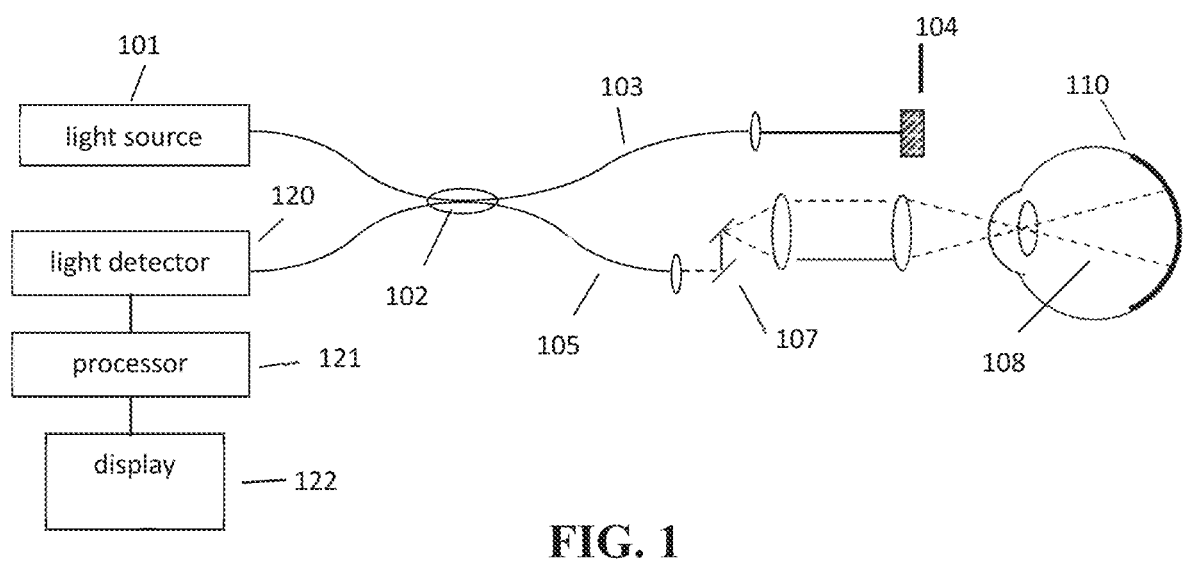
FIG. 1 provides an example of an optical coherence tomography system.

There are several types of ophthalmic images, such as fundus images, optical coherence tomography (OCT), OCT angiography, en face (e.g., an OCT en face image), fluorescein angiography (FA), etc. Each provides different information (or information gathered in a different manner) of an eye, and each may emphasize a different aspect of the eye. Ophthalmic images, in general, are an integral part of diagnosing a particular eye-related malady, or ophthalmic pathology. Diagnoses, however, can be subjective, and dependent upon the level of background knowledge of a physician inspecting a particular ophthalmic image. The present disclosure seeks to use machine learning techniques (e.g. decision tree learning, support vector machines, artificial neural networks (ANN), deep learning, etc.) to aid in the diagnosis of ophthalmic pathologies from an ophthalmic image.

In particular, the present disclosure illustrates the use of a convolutional neural network as a specific example of machine learning due to its facility for learning using images. A convolutional neural network (CNN) is similar to a typical (deep learning) neural network (NN) in that it may have multiple hidden layers; is made up of neurons having learnable weights and biases; and each neuron may receive inputs, perform an operation and be optionally followed by a non-linearity. A convolutional neural network differs from a typical neural network in that the CNN assumes that data close together is more related than data far apart, which permit its architecture to be optimized, making forward functions more efficient and reducing the number of parameters. The use of CNNs have been successfully applied to data such as images and audio.

The convolutional neural network may be trained using a library of previously diagnosed images. For example, the diagnosed images may be selected/extracted from an electronic store of health information such as an electronic health record (EHR) or electronic medical record (EMR). Preferably, each diagnosed image may include a description of its diagnosed malady. Optionally, the specific tissue region (e.g., image region) of the diagnosed image that is associated with the diagnosed malady may be identified for ease of training. Typically, a convolutional neural network may determine for itself what features of an input image to extract for training and testing purposes. In some embodiments, however, it may be desirable to inspect an input test image for specific characteristic features, such as tissue cluster shapes, colors, relative sizes, relative locations, etc. associated with specific ophthalmic maladies. For example, a deformation of the retinal pigment epithelium (RPE) away from the Bruch's membrane may be associated with age-related macular degeneration, a microaneurysm may be associated with diabetic retinopathy (DR), and areas of ischemia may be associated with DR or retinal vein occlusion (RVO). Thus, in addition to identifying potentially abnormal regions in an input test image, it is preferable that the trained CNN further associate at least one specific disease condition with each identified potentially abnormal region.

One or more trained CNNs may be part of, or accessible by, an ophthalmic diagnostic tool or method. The ophthalmic diagnostic tool (which may be implemented in hardware, software, or firmware) may be incorporated into an OCT system, fundus imager, or other stand-alone unit such as a personal computer, handheld computing device, or diagnostic tool. In operation, a test ophthalmic image to be diagnosed and of a specific type (e.g., fundus, OCT, OCT angiography, etc.) is submitted to, acquired by, or otherwise accessed by the ophthalmic diagnostic tool and submitted to a (corresponding) CNN trained on the same type of ophthalmic images. For example, a test ophthalmic OCT angiography image may be submitted to a CNN trained to identify potentially abnormal regions of an ophthalmic (OCT) angiography image. This CNN may be selected from a bank of available CNNs, each trained on a different, respective type of ophthalmic image. The CNNs are preferably further trained to associates at least one, specific abnormality type (e.g., disease, malady, medical condition, etc.) with each identified potentially abnormal region. The submitted test ophthalmic image may then be displayed with any identified potentially abnormal region highlighted. This may be done, for example, by providing a (at least partially transparent) overlay of a specific color covering, and bounded by, the identified potentially abnormal region of the submitted test image. If multiple potentially abnormal regions associated with multiple different abnormality types are identified, then the highlighting may be color coded according to associated abnormality type.

The ophthalmic diagnostic tool (or the CNN) may maintain, or otherwise have access to, a diagnostic library of diagnosed ophthalmic samples. Preferably, the diagnostic library has at least one diagnosed ophthalmic sample associated with, or linked to, each abnormality type identifiable by the CNN. Each diagnosed ophthalmic sample in the library may include at least one sample image, textual information, and/or link to additional information related to a particular abnormality type, such as diabetic retinopathy, glaucoma, central retinal artery occlusion, micro-aneurysms, neovascularization, soft or hard exudates, hemorrhages, etc. The ophthalmic diagnostic tool may respond to a user-selection of a highlighted region by displaying a diagnosed ophthalmic sample related to the specific abnormality type corresponding to the highlighted region. The displayed diagnosed ophthalmic sample may be from the diagnostic library.

In embodiments, the ophthalmic diagnostic tool or method may be incorporated into an ophthalmic imaging device such as a fundus imager or OCT system, or may be provided as a network-accessible service. For example, the ophthalmic diagnostic tool may be implemented as an application executable on a mobile device, such as computing tablet or smart phone, that accesses a remote host over the Internet, and the remote host provides the ophthalmic image diagnosing service. In this manner, higher computing requirements may be offloaded from the mobile device onto the remote host. Alternatively, the diagnostic tool may be provided entirely on the Internet as a website accessible over the Internet by use of a web browser. In this manner a physician may make use of the present ophthalmic diagnostic services from anywhere using any device having Internet access and capable of running a web browser.

There are several different types of ophthalmic images. For example, ophthalmic images may be created by fundus photography, fluorescein angiography (FA), fundus autofluorescence (FAF), optical coherence tomography (OCT), OCT angiography (OCTA), ocular ultrasonography, microperimetry and/or electroretinography (ERG). In embodiments, the present machine learning module may be training using diagnosed samples from one, or a combination of, or all ophthalmic image types. Examples of fundus imagers are provided in U.S. Pat. Nos. 8,967,806 and 8,998,411, and examples of an OCT are provided in U.S. Pat. Nos. 6,741,359 and 9,706,915, all of which are herein incorporated in their entirety by reference. In embodiments, the present disclosure may be particularly optimized to diagnose OCT angiography (OCTA) images. Examples of an OCTA imaging system may be found in U.S. Pat. Nos. 9,700,206 and 9,759,544, both of which are herein incorporated in their entirety by reference.

FIG. 1 provides an example of an optical coherence tomography system, which may be used to provide an OCTA image. Light from a light source 101 is routed, typically by optical fiber 105, to illuminate a sample 110, such as tissues in a human eye. The source 101 can be either a broadband light source with short temporal coherence length in the case of SD-OCT or a wavelength tunable laser source in the case of SS-OCT. The light is scanned, typically with a scanner 107 between the output of the fiber and the sample, so that the beam of light (dashed line 108) is scanned laterally (e.g., in x and/or y directions) over the area or volume to be imaged. Light scattered from the sample is collected, typically into the same fiber 105 used to route the light for sample illumination. Reference light derived from the same source 101 travels a separate path, in this case involving fiber 103 and retro-reflector 104 with an adjustable optical delay. Those skilled in the art will recognize that a transmissive reference path can also be used and that the adjustable delay may be placed in the sample or reference arm of the interferometer. Collected sample light is combined with reference light, typically in a fiber coupler 102, to form light interference in a detector 120. Although a single fiber port is shown going to the detector, those skilled in the art will recognize that various designs of interferometers can be used for balanced or unbalanced detection of the interference signal. The output from the detector is supplied to a processor (or computing system) 121. The results can be stored in the processor 121 or displayed on display 122. The processing and storing functions may be localized within the OCT instrument or functions may be performed on an external processing unit to which the collected data is transferred. This unit could be dedicated to data processing or perform other tasks which are quite general and not dedicated to the OCT device. The processor 121 may contain, for example, a field-programmable gate array (FPGA), a digital signal processor (DSP), an application specific integrated circuit (ASIC), one or more general purpose graphic processing unit (GPGPU), a system-on-chip (SoC), or a combination thereof. The processor 121 may perform some, or the entire angiography data processing steps, prior to passing on to a host processor or in a parallelized fashion. Optionally, the angiography data may be submitted to a machine learning module internal to, or remote from, processor 121 for diagnosis purposes, as described below.

The sample and reference arms in the interferometer could consist of bulk-optics, fiber-optics, or hybrid bulk-optic systems and could have different architectures such as Michelson, Mach-Zehnder or common-path based designs as would be known to those skilled in the art. Light beam as used herein may be any carefully directed light path. In time-domain systems, the reference arm may have a tunable optical delay to generate interference. Balanced detection systems are typically used in TD-OCT and SS-OCT systems, while spectrometers are used at the detection port for SD-OCT systems. The invention described herein could be applied to any type of OCT system capable of generating data for OCT angiography analysis including spot scanning, multi-spot scanning, or partial field and full field imaging systems. The techniques described herein (including the diagnosing capabilities of the present application) could be applicable to any body parts, for example eye (both anterior and posterior chambers), skin, brain, muscle, cochlear, and internal organs if integrated with endoscope or catheter probe.

In Fourier Domain optical coherence tomography (FD-OCT), each measurement is the real-valued spectral interferogram (Sj(k)). The real-valued spectral data typically goes through several post-processing steps including background subtraction, dispersion correction, etc. The Fourier transform of the processed interferogram, results in a complex valued OCT signal output $Aj(z)=|Aj|ei\varphi$. The absolute value of this complex OCT signal, $|Aj|$, reveals the profile of scattering intensities at different path lengths, and therefore scattering as a function of depth (z-direction) in the sample. Similarly, the phase, $\varphi j$ can also be extracted from the complex valued OCT signal. The profile of scattering as a function of depth is called an axial scan (A scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. The term "cluster scan" may refer to a single unit or block of data generated by repeated acquisitions at the same location for the purposes of analyzing motion contrast. A cluster scan can consist of multiple A-scans or B-scans collected over time at approximately the same location(s) on the sample. A variety of ways to create B-scans are known in the art including but not limited to along the horizontal or x-direction, along the vertical or y-direction, along the diagonal of x and y, or in a circular or spiral pattern. B-scans may be in the x-z dimensions but may be any cross sectional image that includes the z-dimension.

In OCT Angiography, or Functional OCT, analysis algorithms may be applied to OCT data collected at the same, or approximately the same, sample locations on a sample at different times to analyze motion or flow (see for example US Patent Publication Nos. 2005/0171438, 2012/0307014, 2010/0027857, 2012/0277579 and U.S. Pat. No. 6,549,801, all of which are hereby incorporated in their entirety by reference). Motion contrast analysis techniques can be applied to the intensity information derived from the image data, the phase information from the image data, and/or the complex image data. An en face vasculature image is an image displaying motion contrast signal in which the data dimension corresponding to depth is displayed as a single representative value, typically by summing or integrating all or an isolated portion of the data (see for example U.S. Pat. No. 7,301,644 hereby incorporated in its entirety by reference).

Figure 2:
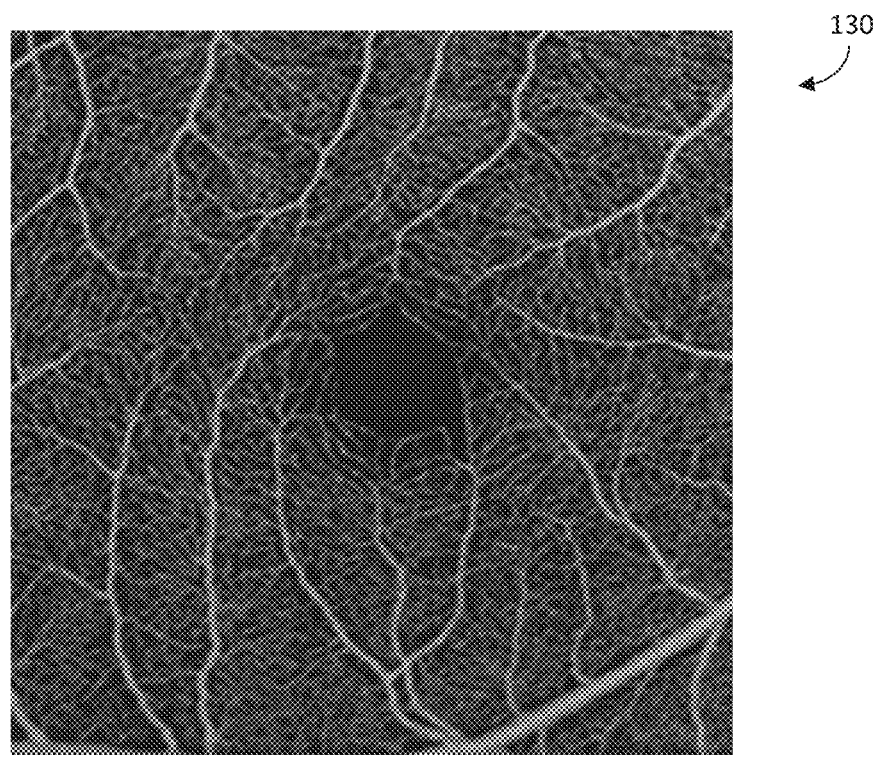
FIG. 2 shows an example of an en face vasculature image, such as those generated by an OCT system.

FIG. 2 shows an example of an en face vasculature image 130. After processing the data to highlight motion contrast using any of the motion contrast techniques known in the art, a range of pixels corresponding to a given tissue depth from the surface of internal limiting membrane (ILM) in retina, may be summed to generate the en face (e.g., frontal view) image 130 of the vasculature.

As stated above, the present disclosure may use a machine learning module that is trained to preferably identify ophthalmic maladies based on a collection of diagnosed examples, e.g., diagnosed images. Examples of machine learning (ML) architectures (or models or algorithms) include: nearest neighbor, naive Bayes, decision trees, linear regression, support vector machines (SVM), neural networks, etc. For exemplary purposes, the present discloser recites a machine learning module based on neural networks. More specifically, a convolutional neural network (CNN) may be used for its facility to be trained using images, but other machine learning techniques may also be used.

Before discussing the present embodiments in detail, it may be beneficial to first provide some background information regarding neural networks in general, and convolutional neural networks in particular. A neural network, or neural net, is a (nodal) network of interconnected neurons, where each neuron represents a node in the network. Groups of neurons may be arranged in layers, with the outputs of one layer feeding forward to a next layer in a multilayer perception (MLP) arrangement. MLP may be understood to be a feedforward neural network model that maps a set of input data onto a set of output data.

Figure 3:
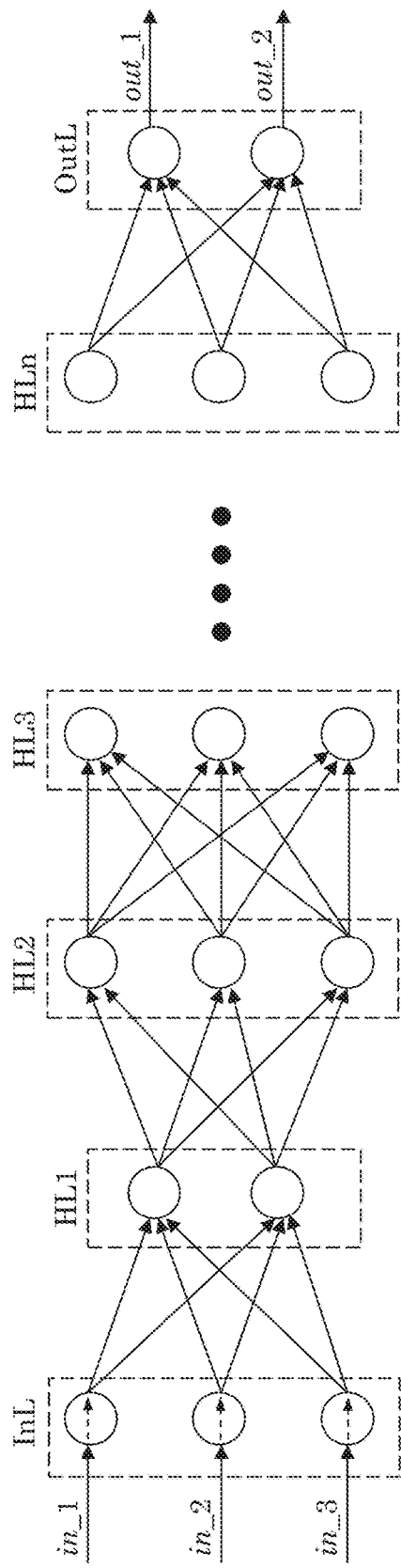
FIG. 3 illustrates an example of a multilayer perception (MLP) neural network.

FIG. 3 illustrates an example of a multilayer perception (MLP) neural network. Its structure may include multiple hidden (e.g., internal) layers HL1 to HLn that map an input layer InL (that receives a set of inputs (or vector input) in_1 to in_3) to an output layer OutL that produces a set of outputs (or vector output), e.g., out_1 and out_2. Each layer may have any given number of nodes, which are herein illustratively shown as circles within each layer. In the present example, the first hidden layer HL1 has two nodes, while hidden layers HL2, HL3, and HLn each have three nodes. Generally, the deeper the MLP (e.g., the greater the number of hidden layers in the MLP), the greater its capacity to learn. The input layer InL receives a vector input (illustratively shown as a three-dimensional vector consisting of in_1, in_2 and in_3), and may apply the received vector input to the first hidden layer HL1 in the sequence of hidden layers. An output layer OutL receives the output from the last hidden layer, e.g., HLn, in the multilayer model, processes its inputs, and produces a vector output result (illustratively shown as a two-dimensional vector consisting of out_1 and out_2).

Typically, each neuron (or node) produces a single output that is fed forward to neurons in the layer immediately following it. But each neuron in a hidden layer may receive multiple inputs, either from the input layer or from the outputs of neurons in an immediately preceding hidden layer. In general, each node may apply a function to its inputs to produce an output for that node. Nodes in hidden layers (e.g., learning layers) may apply the same function to their respective input(s) to produce their respective output(s). Some nodes, however, such as the nodes in the input layer InL receive only one input and may be passive, meaning that they simply relay the values of their single input to their output(s), e.g., they provide a copy of their input to their output(s), as illustratively shown by dotted arrows within the nodes of input layer InL.

Figure 4:
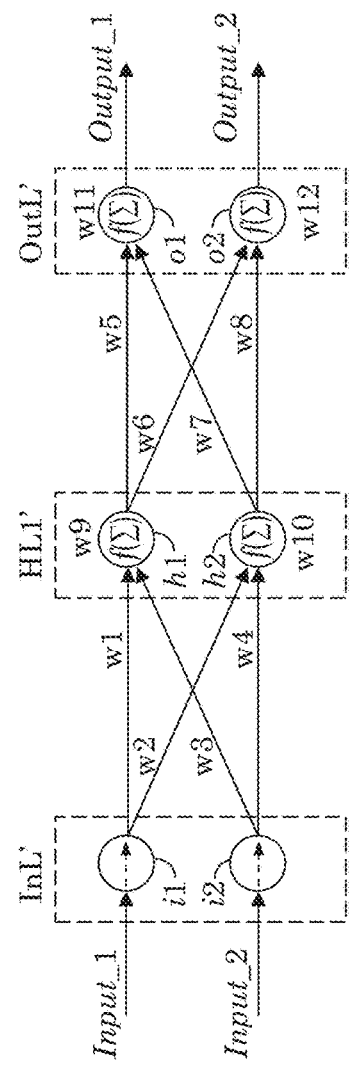
FIG. 4 shows a simplified neural network consisting of an input layer, a hidden layer, and an output layer.

For illustration purposes, FIG. 4 shows a simplified neural network consisting of an input layer InL', a hidden layer HL1', and an output layer OutL'. Input layer InL' is shown having two input nodes i1 and i2 that respectively receive inputs Input_1 and Input_2 (e.g. the input nodes of layer InL' receive an input vector of two dimensions). The input layer InL' feeds forward to one hidden layer HL1' having two nodes h1 and h2, which in turn feeds forward to an output layer OutL' of two nodes o1 and o2. Interconnections, or links, between neurons (illustrative shown as solid arrows) have weights w1 to w8. Typically except for the input layer, a node (neuron) may receive as input the outputs of nodes in its immediately preceding layer. Each node may calculate its output by multiplying each of its inputs by each input's corresponding interconnection weight, summing the products of it inputs, adding (or multiplying by) a constant defined by another weight or bias that may associated with that particular node (e.g., node weights w9, w10, w11, w12 respectively corresponding to nodes h1, h2, o1, and o2), and then applying a non-linear function or logarithmic function to the result. The non-linear function may be termed an activation function or transfer function. Multiple activation functions are known the art, and selection of a specific activation function is not critical to the present discussion. It is noted, however, that operation of the ML model, or behavior of the neural net, is dependent upon weight values, which may be learned so that the neural network provides a desired output for a given input.

The neural net learns (e.g., is trained to determine) appropriate weight values to achieve a desired output for a given input during a training, or learning, stage. Before the neural net is trained, the weights may be individually assigned an initial (e.g., random and optionally non-zero) value. Various methods of assigning initial weights are known in the art. The weights are then trained (optimized) so that for a given training vector input, the neural network produces an output close to a desired (predetermined) training vector output. For example, the weights may be incrementally adjusted in thousands of iterative cycles by a technique termed back-propagation. In each cycle of back-propagation, a training input (e.g., vector input) is fed forward through the neural network to determine its actual output (e.g., vector output). An error for each output neuron, or output node, is then calculated based on the actual neuron output and a target training output for that neuron. One then propagates back through the neural network (in a direction from the output layer back to the input layer) updating the weights based on how much effect each weight has on the overall error so that the output of the neural network moves closer to the desired training output. This cycle is then repeated until the actual output of the neural network is within an acceptable error range of the desired training output for the given training input.

Thus, construction of a neural network model may include a learning (or training) stage and a classification (or operational) stage. In the learning stage, the neural network may be trained for a specific purpose and may be provided with a set of training examples, including training (sample) inputs and training (sample) outputs, and optionally including a set of validation examples to test the progress of the training. During this learning process, various weights associated with nodes and node-interconnections in the neural network are incrementally adjusted in order to reduce an error between an actual output of the neural network and the desired training output. In this manner, a multi-layer feedforward neural network (such as discussed above) may be made capable of approximating any measurable function to any desired degree of accuracy. The result of the learning stage is a (neural network, machine learning) model that has been learned (e.g., trained). In the operational stage, a set of test inputs (or live inputs) may be submitted to the learned (trained) ML model, which may apply what it has learned to produce an output prediction based on the test inputs.

Like the regular neural networks of FIGS. 3 and 4, convolutional neural networks are also made up of neurons that have learnable weights and biases. Each neuron receives inputs, performs an operation (e.g., dot product), and is optionally followed by a non-linearity. The CNN, however, may receive raw image pixels at one end (e.g., the input end) and provide classification (or class) scores at the other end (e.g., the output end). Because CNNs expect an image as input, they are optimized for working with volumes (e.g., pixel height and width of an image, plus the depth of the image, e.g., color depth such as an RGB depth defined of three colors: red, green, and blue). For example, the layers of a CNN may be optimized for neurons arranged in 3 dimensions. The neurons in a CNN layer may also be connected to a small region of the layer before it, instead of all of the neurons in a fully-connected NN. The final output layer of a CNN may reduce a full image into a single vector (classification) arranged along the depth dimension.

Figure 5:
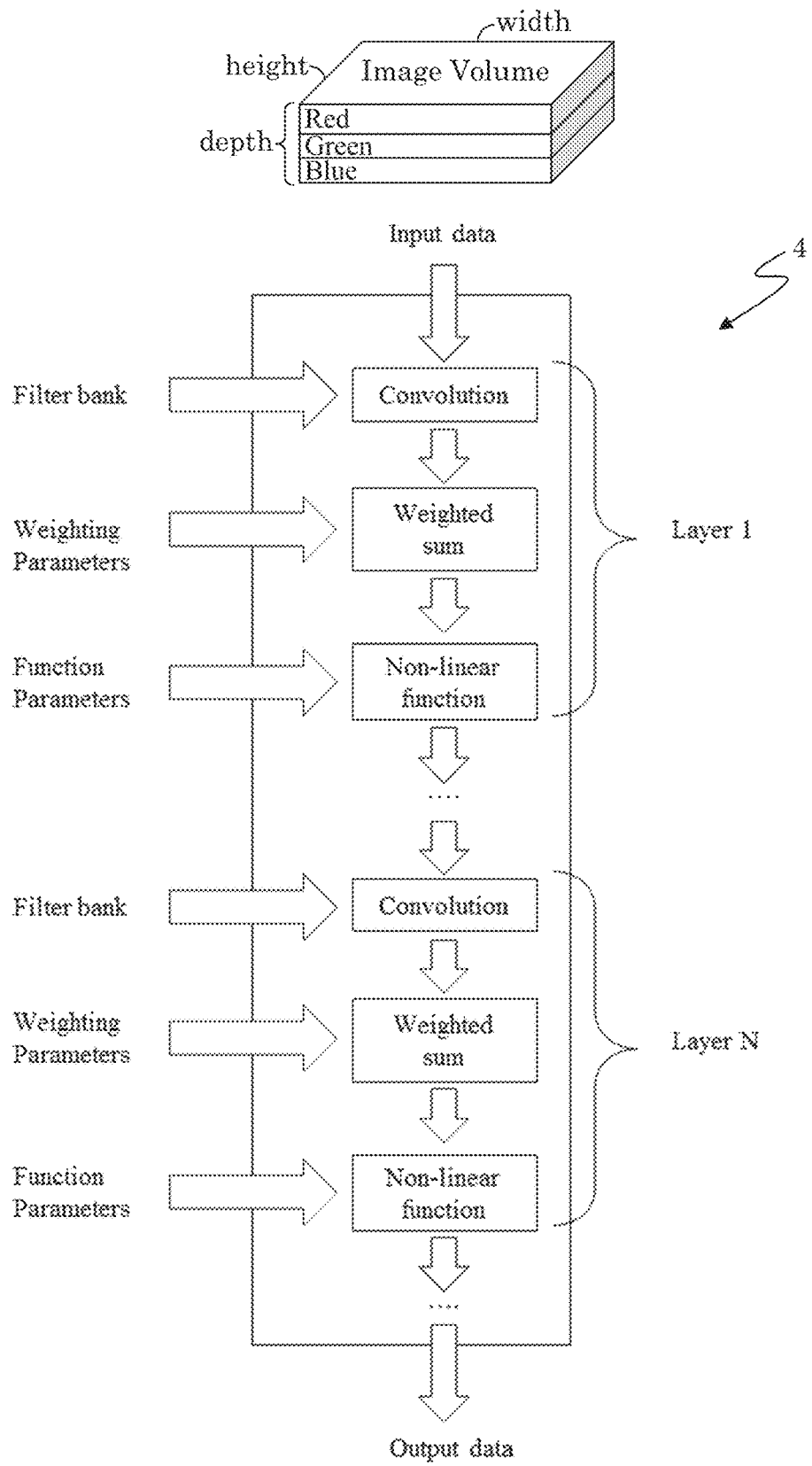
FIG. 5 provides an example convolutional neural network architecture.

FIG. 5 provides an example convolutional neural network architecture. A convolutional neural network 4 may be defined as a sequence of 2 or more layers (e.g., Layer 1 to Layer N), where a layer may include a (image) convolution step, a weighted sum (of results) step, and a non-linear function step. Each layer and component of a layer may have different pre-determined filters (from a filter bank), weights (or weighting parameters), and/or function parameters. In the present example, the input data is an image, which may be raw pixel values of the image, of a given pixel height and width. In the present example, the input image is illustrated as having a depth of three color channels RGB (Red, Green, and Blue). Optionally, the input image may undergo various preprocessing, and the preprocessing results may be input in place of, or in addition to, the raw input image. Some examples of image preprocessing may include: retina blood vessel map segmentation, color space conversion, adaptive histogram equalization, connected components generation, etc. As explained above, the CNN may be trained with multiple examples of diagnosed images (e.g., ophthalmic images), but the CNN may also be trained to identify specific image regions/segments illustrating specific symptoms of maladies, depending upon the input data to the CNN. For example, the CNN may be trained to identify damaged blood vessels, blood clots, narrow blood vessels, etc. Within a layer, a dot product may be computed between their given weights and a small region they are connected to in the input volume. Many ways of configuring a CNN are known in the art, but as an example, a layer may be configured to apply an elementwise activation function, such as max(0,x) thresholding at zero. A pooling function may be performed (e.g., along the x-y directions) to down-sample a volume. Additionally, a fully-connected layer may be used to determine the classification output and produce a one-dimensional output vector.

After the CNN has been trained, in operation the trained CNN may receive an input ophthalmic image, and identify any region within the input ophthalmic image that is potentially abnormal (e.g., similar to one of the training diagnosed sample), and associate with each identified potentially abnormal region one or more possible maladies. These possible maladies may further be ranked by probability of being a match.

Thus, irrespective of the machine learning algorithm used, embodiments of the present invention further provide a graphical interface that highlights regions of an input test image (e.g. within an input OCT or OCTA dataset) that are deemed to be diseased, suspicious, or simply not-normal. In embodiments, the identified regions may not be specific to a single identifiable ophthalmic feature such as drusen, fluid, geographic atrophy (GA), thickness, etc.

FIG. 6 illustrates an operational flow in accord with the present invention, including a graphical user interface (GUI) output. In the present example, a test input image 2 is submitted to a trained convolutional neural network (CNN) 4 for processing. The output of trained CNN 4 is an output image 6 similar to input image 2 with an overlay identifying normal areas 8 and potentially abnormal regions 10 (e.g., areas categorized as 'diseased' or 'suspicious'). The potentially abnormal regions 10 may be highlighted in a color different from the normal areas 8. The graphic user interface may further show (e.g. display or bring up) additional areas similar to the highlighted regions, e.g., region 10, from previous scans (or from a pre-defined Atlas, or library, or database).

Figure 7:
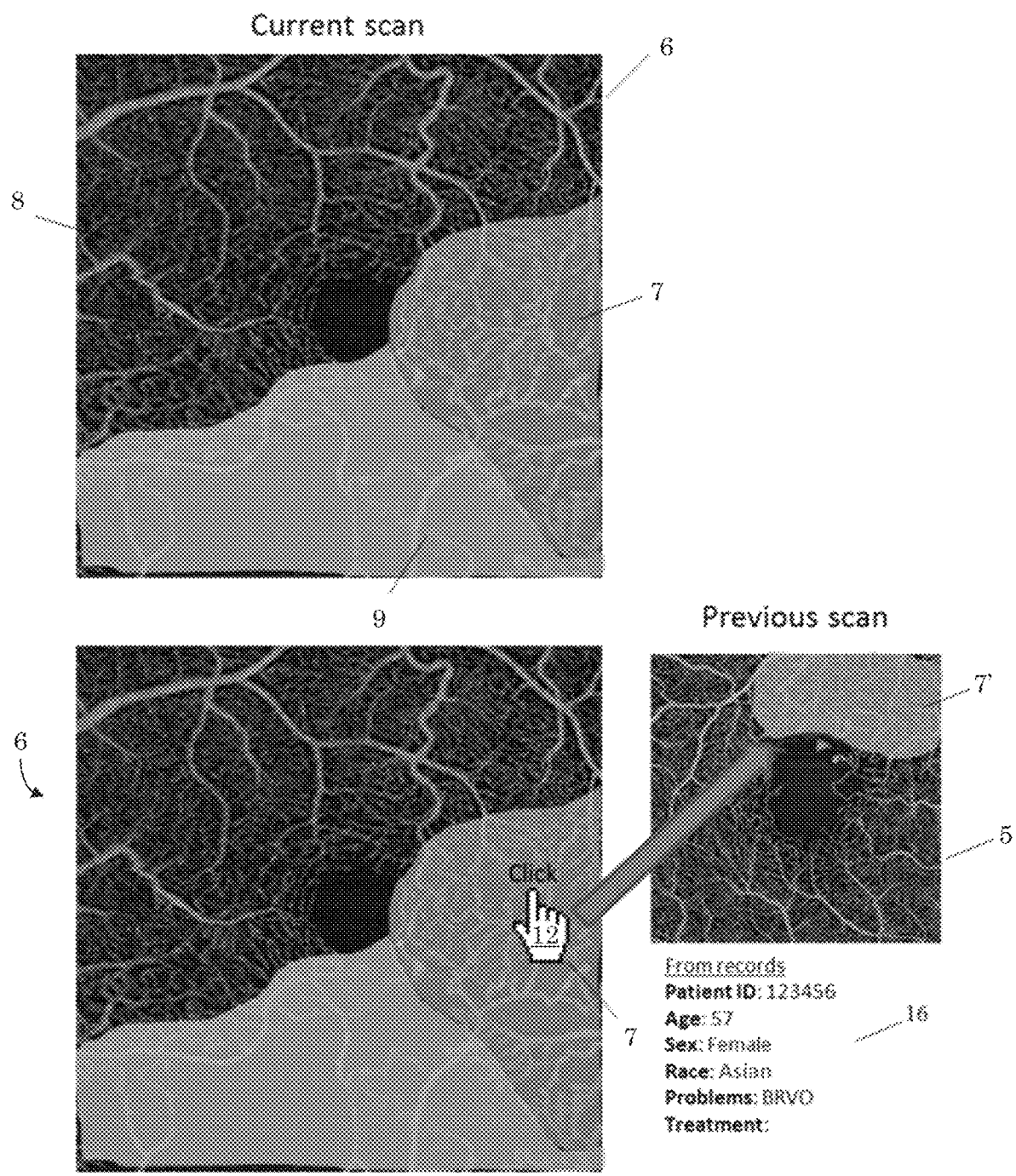
FIG. 7 illustrate a graphical user interface that responds to a user input by displaying additional examples of diagnosed tissue similar to a highlighted region.

FIG. 7 illustrate a graphical user interface that responds to a user input by displaying additional examples of diagnosed tissue similar to a highlighted region. The top image is another example of an output image 6, such as from CNN 4 of FIG. 6. The top image may be from an input image of a current (or archived) OCTA en face scan. As before, output image 6 has an overlay identifying normal areas 8 and highlighting any potentially abnormal regions. In the present example, two potentially abnormal regions 7 and 9 are identified. The highlighting color may be color coded according to the specific malady associated with each potentially abnormal region. Therefore, potentially abnormal regions 7 and 9 are each highlighted differently (e.g., assigned a different color) indicating that region 7 is associated with a malady different than that associated with region 9.

The bottom portion of FIG. 7 depicts the response due to a user-input selecting one of the highlighted regions 7 or 9. In the present case, input curser 12 of the user interface shows that in response to a user clicking on highlighted region 7, a secondary (or previous) scan 5 with a similarly-diseased (and highlighted) region 7' is brought up and displayed. The highlighted region 7' in the previous scan 5 that was similar to region 7 in the current scan 6 is also highlighted and the previous patient's (textual) record 16 is also fetched and displayed from the saved records (e.g., from an EMR), such as what would be stored on the scanning device or in the patient's electronic medical record. In some embodiments, a manual click may need not be required, and the previous scans may be brought up and displayed automatically. The brought up records may further be extracted from a local or remote diagnostic Atlas (or library) of diagnosed sample images. The previous scan may be from a different patient, or in some instances, data from the same patient from a past visit may be shown if the algorithm deems it useful. One such useful instance to show a scan of the same patient from a different visit would be if the patient improved then declined back to a previous level.

In embodiments, the displayed secondary scan 5 may include selectable links to additional diagnostic information. For example, clicking on highlighted region 7 of output image 6 may result in only secondary scan 5 with region 7' being displayed, and textual record 16 not being initially displayed. In this case, the textual record 16 may be displayed in response to the user clicking a non-highlighted region of secondary scan 5. Alternatively, the displayed secondary scan 5 may include selectable links to other sample images associated with the highlighted region 7 of the output image 6. For example, selecting highlighted region 7' of secondary scan 5 may result in a tertiary scan sample (not shown) being displayed. The tertiary scan sample may be associated with region 7 output image 6 or alternatively be associated with the selected highlighted region 7' of secondary scan 5.

In embodiments, the graphic user interface may respond to a user-selection of highlighted region 7 of output image 6 by displaying a selection of potential diagnoses (e.g. pathologies or abnormality types) associated with the highlighted region 7. The selection of potential diagnoses may be arranged by probability, e.g., as determined by trained CNN 4. In this case, user-selection of one of the potential diagnosis results may result in displaying a secondary scan (e.g., secondary scan 5) associated with the selected diagnosis.

FIG. 8 illustrates an overview of ophthalmic image diagnostic system in accord with some embodiments of the present invention. In the present embodiment, a computing system, or device, 11 may extract ophthalmic image information from various sources, such as from an ophthalmic imager 17 (e.g., an OCT system or fundus imager) or from a patient's medical record (e.g., from EMR 13). Optionally, computing device 11 may be a hand-held device, integrated into an ophthalmic diagnostic tool/imager, or embodied within a computer-readable non-transitory storage media. In some embodiments, computing device 11 may incorporate a web-based application (or "app"), and may interface with one or more electronic medical record (EMR) systems 13, either directly or over a computer network. For example, the web-based application may access a patient's EMR data (e.g. access ophthalmic image data) from EMR 13 over the Internet 15 for analysis.

Computing device 11 may have direct access to ophthalmic imager 17, as illustrated by solid arrow 19, or may access ophthalmic imager 17 over the Internet 15, as illustrated by dotted arrow 20. For example, solid arrow 19 may represent a direct wired or wireless connection, such as a wired connection over a local area network, Wi-Fi access to the local area network, a Bluetooth connection, or a USB interface.

As explained above, an input ophthalmic image may be submitted to a trained convolutional neural network that highlights potentially abnormal regions and provides examples of previously diagnosed image samples similar to the highlighted regions. Computing device 11 may hold the trained convolutional neural network and access diagnosed samples from an internal library or from a remote diagnostic library (or atlas) 18 of diagnosed samples. Alternatively, the convolutional neural network may be maintained and provided as an online diagnostic service 21. In this case, computing device 11 may provide an interface (e.g., a web browser) for accessing diagnostic service 21, for submitting a test ophthalmic image to diagnostic service 21, and for retrieving analyzed results with highlighted regions from diagnostic service 21. In this scenario, diagnostic service 21 may maintain diagnostic library 18 or may access it remotely.

Figure 9:
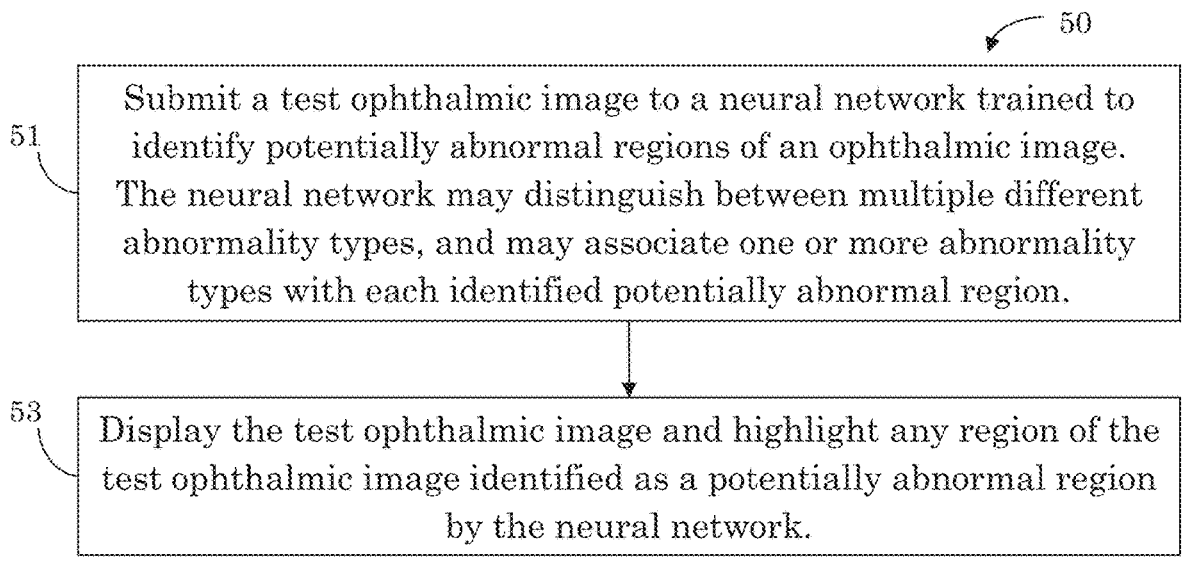
FIG. 9 illustrates an example method for ophthalmic image diagnostics.

FIG. 9 illustrates an example method 50 for ophthalmic image diagnostics. The method may begin at step 51, where a test ophthalmic image (e.g., OCT image, OCTA image, fundus image, B-scan image, FA image, etc.) is submitted to a (convolutional) neural network trained to identify potentially abnormal regions of an ophthalmic image. The neural network (or other machine learning model/algorithm) may distinguish between multiple different abnormality types (diagnosis, maladies, pathologies), and may also associate one or more abnormality types with each identified potentially abnormal region. At step 53, the test ophthalmic image is displayed (on a display) and any region of the test ophthalmic image identified as a potentially abnormal region by the neural network is highlighted.

Figure 10:
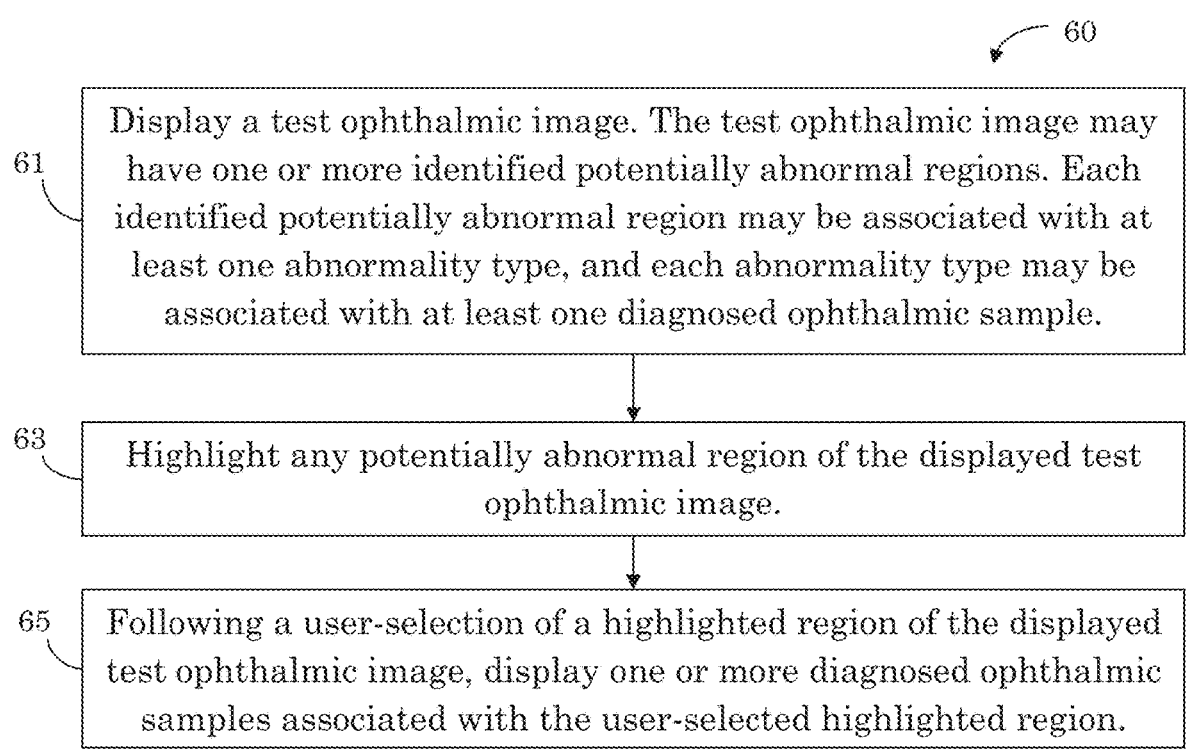
FIG. 10 illustrates another example method for ophthalmic image diagnostic.

FIG. 10 illustrates another example method 60 for ophthalmic image diagnostic. The method may begin at step 61, where a test ophthalmic image (e.g., OCT image, OCTA image, fundus image, B-scan image, FA image, etc.) is displayed (on a display). The test ophthalmic image may have one or more identified potentially abnormal regions, and each identified potentially abnormal region may be associated with at least one abnormality type (diagnosis, maladies, pathologies). Each abnormality type may further be associated with at least one (previously) diagnosed ophthalmic sample. At step 63, any identified potentially abnormal region of the displayed test ophthalmic image is highlighted. At step 65, following (or in response to) a user-selection of a highlighted region of the displayed test ophthalmic image, one or more diagnosed ophthalmic samples associated with the user-selected highlighted region is displayed.

Some embodiments may repeat one or more steps of the methods of FIGS. 9 and 10, where appropriate. Although this disclosure describes and illustrates particular steps of the methods of FIGS. 9 and 10 as occurring in a particular order, this disclosure contemplates any suitable steps of the methods of FIGS. 9 and 10 occurring in any suitable order.

Figure 11:
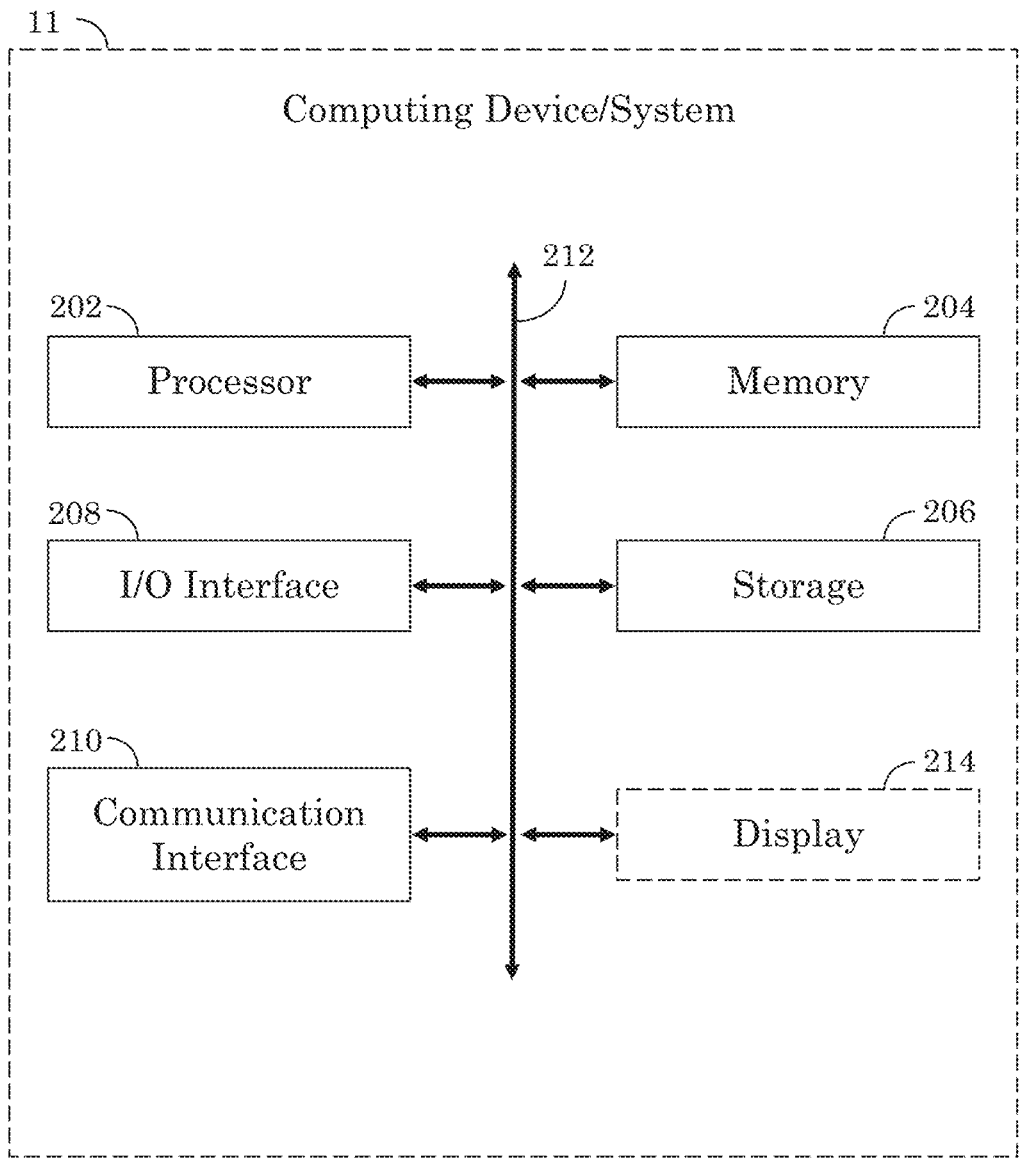
FIG. 11 illustrates an example computer device (or computer system).

FIG. 11 illustrates an example computer device (or computer system), e.g. 11 and/or 121. In some embodiments, one or more computer systems may perform one or more steps of the methods of FIGS. 9 and 10. The computer system may take any suitable physical form. For example, the computer system may be an embedded computer system, a system-on-chip (SOC), a single-board computer system (SBC) (such as, for example, a computer-on-module (COM) or system-on-module (SOM)), a desktop computer system, a laptop or notebook computer system, a mesh of computer systems, a mobile telephone, a personal digital assistant (PDA), a server, a tablet computer system, or a combination of two or more of these. Where appropriate, the computer system may reside in a cloud, which may include one or more cloud components in one or more networks.

In some embodiments, the computer system includes a processor 202, memory 204, storage 206, an input/output (I/O) interface 208, a communication interface 210, and a bus 212. The computer system may optionally also include a display 214, such as a computer monitor or screen. Processor 202 includes hardware for executing instructions, such as those making up a computer program. For example, processor 202 may be a central processing unit (CPU) or a general-purpose computing on graphics processing unit (GPGPU). Memory 204 may include main memory for storing instructions for processor 202 to execute or to hold interim data during processing. For example, memory 204 may include random access memory (RAM), such as dynamic RAM (DRAM) or static RAM (SRAM). In some embodiments, storage 206 may include long-term or mass storage for data or instructions. For example, storage 206 may include a disk drive (HDD or SSD), flash memory, ROM, EPROM, or other type of non-volatile memory. I/O interface 208 may include one or more interfaces for communication with I/O devices, which may enable communication with a person (e.g., user). Communication interface 210 may provide network interfaces for communication with other systems or networks. For example, communication interface 210 may include a network interface controller (NIC) and/or a wireless NIC for communication with another computer system on a network. Communication interface 210 may further include a Bluetooth interface or other type of packet-based communication. Bus 212 may provide a communication link between the above mentioned components of the computing system.

While the invention has been described in conjunction with several specific embodiments, it will be evident to those skilled in the art that many further alternatives, modifications, and variations will be apparent in light of the foregoing description. Thus, the invention described herein is intended to embrace all such alternatives, modifications, applications and variations as may fall within the spirit and scope of the appended claims.

The invention claimed is:

1. An ophthalmic image diagnostic method, comprising:
submitting a test ophthalmic image to a neural network trained to identify potentially abnormal regions of an ophthalmic image, the neural network distinguishing between one or more abnormality types, wherein at least one abnormality type is associated with each identified potentially abnormal region;
displaying the test ophthalmic image on a display and highlighting on the display a region of the test ophthalmic image identified as a potentially abnormal region; and
displaying on the display at least one diagnosed ophthalmic sample associated with the abnormality type corresponding to the highlighted potentially abnormal region, wherein the test ophthalmic image is of a first patient and the displayed diagnosed ophthalmic sample is of different patient.

2. An ophthalmic image diagnostic method, comprising:
submitting a test ophthalmic image to a neural network trained to identify potentially abnormal regions of an ophthalmic image, the neural network distinguishing between a plurality of abnormality types, wherein the neural network associates at least one abnormality type with each identified potentially abnormal region;
displaying the test ophthalmic image on a display and highlighting on the display any region of the test ophthalmic image identified as a potentially abnormal region by the neural network;
providing access to a diagnostic library, the diagnostic library having at least one diagnosed ophthalmic sample associated with each of the plurality of abnormality types; and
responding to a user-selection of a highlighted region of the displayed test ophthalmic image by displaying at least one diagnosed ophthalmic sample, from the diagnostic library, associated with the abnormality type corresponding to the selected highlighted region.

3. The method of claim 2, wherein the displayed, at least one diagnosed ophthalmic sample includes at least one link to another diagnosed ophthalmic sample, from the library, associated with the abnormality type corresponding to the selected highlighted region.

4. The method of claim 1, wherein each highlighted region on the displayed test ophthalmic image is color-coded according to its associated abnormality type.

5. The method of claim 1, wherein the displayed, at least one diagnosed ophthalmic sample includes a sample tissue image representative of the associated abnormality type.

6. The method of claim 1, wherein:
the displayed, at least one diagnosed ophthalmic sample includes a sample tissue image; and
a portion of the sample tissue image that is most similar to the highlighted region of the displayed test ophthalmic image is highlighted.

7. The method of claim 6, further including:
responding to a user-selection of the highlighted portion of the sample tissue image by displaying a second diagnosed ophthalmic sample.

8. The method of claim 1, wherein:
the test ophthalmic image is of a first patient;
the displayed at least one diagnosed ophthalmic sample is of said first patient; and
the displayed at least one diagnosed ophthalmic sample includes a tissue image with a highlighted portion corresponding to the highlighted region of the displayed test ophthalmic image.

9. The method of claim 1, wherein the displayed, at least one diagnosed ophthalmic sample includes a textual description of the associated abnormality type.

10. The method of claim 1, wherein the displayed, at least one diagnosed ophthalmic sample includes a selectable link to additional diagnostic information.

11. The method of claim 1, wherein the test ophthalmic image includes one or more of an optical coherence tomography (OCT) image, an OCT Angiography image, and an en face ophthalmic image.

12. An ophthalmic image diagnostic method, comprising:
displaying a test ophthalmic image on a display, the test ophthalmic image having at least one identified potentially abnormal region, each identified potentially abnormal region being associated with at least one abnormality type, and each abnormality type being further associated with at least one diagnosed ophthalmic sample;
highlighting on the display any potentially abnormal region of the test ophthalmic image; and
following a user-selection of a highlighted region of the displayed test ophthalmic image, displaying at least one diagnosed ophthalmic sample associated with the selected highlighted region, wherein the test ophthalmic image is of a first patient and the displayed diagnosed ophthalmic sample is of different patient.

13. The method of claim 12, further comprising:
prior to displaying the diagnosed ophthalmic sample, responding to the user-selection of the highlighted region of the displayed test ophthalmic image by displaying a selection of abnormality types associated with the selected highlighted region; and the displayed diagnosed ophthalmic sample is further associated with a user-selection of one of the displayed abnormality types.

14. An ophthalmic image diagnostic method, comprising:
displaying a test ophthalmic image on a display, the test ophthalmic image having at least one identified potentially abnormal region, each identified potentially abnormal region being associated with at least one abnormality type, and each abnormality type being further associated with at least one diagnosed ophthalmic sample;
highlighting on the display any potentially abnormal region of the test ophthalmic image;
following a user-selection of a highlighted region of the displayed test ophthalmic image, displaying at least one diagnosed ophthalmic sample associated with the selected highlighted region; and
prior to highlighting any potentially abnormal region on the display:
submitting the test ophthalmic image to a neural network trained to identify potentially abnormal regions of an ophthalmic image, the neural network distinguishing between a plurality of abnormality types and having access to a library of diagnosed ophthalmic samples associated each abnormality type, wherein the neural network identifies the at least one potentially abnormal region of the test ophthalmic image and associates at least one abnormality type with each identified potentially abnormal region.

15. An ophthalmic image diagnostic system comprising:
one or more processors; and
one or more computer-readable non-transitory storage media coupled to one or more of the processors and comprising instructions operable when executed by one or more of the processors to cause the system to:
submit a test ophthalmic image to a neural network trained to identify potentially abnormal regions of an ophthalmic image, the neural network distinguishing between one or more abnormality types, wherein the neural network associates at least one abnormality type with each identified potentially abnormal region;
display the test ophthalmic image on a display and highlight on the display any region of the test ophthalmic image identified as a potentially abnormal region by the neural network; and
respond to a user-selection of a highlighted region of the displayed test ophthalmic image by displaying at least one diagnosed ophthalmic sample associated with the abnormality type corresponding to the selected highlighted region, wherein the test ophthalmic image is of a first patient and the displayed diagnosed ophthalmic sample is of different patient the displayed ophthalmic sample being different from the test ophthalmic image.

16. An ophthalmic image diagnostic system comprising:
one or more processors; and
one or more computer-readable non-transitory storage media coupled to one or more of the processors and comprising instructions operable when executed by one or more of the processors to cause the system to:
submit a test ophthalmic image to a neural network trained to identify potentially abnormal regions of an ophthalmic image, the neural network distinguishing between a plurality of abnormality types, wherein the neural network associates at least one abnormality type with each identified potentially abnormal region;
display the test ophthalmic image on a display and highlight on the display any region of the test ophthalmic image identified as a potentially abnormal region by the neural network
provide access to a diagnostic library, the diagnostic library having at least one diagnosed ophthalmic sample associated with each of the plurality of abnormality types; and
respond to a user-selection of a highlighted region of the displayed test ophthalmic image by displaying at least one diagnosed ophthalmic sample, from the diagnostic library, associated with the abnormality type corresponding to the selected highlighted region.

17. The system of claim 16, wherein:
the display is part of a computing device remote from the diagnostic library;
the computing device retrieves the at least one diagnostic ophthalmic sample over a computer network in response to the user-selection of the highlighted region of the displayed test ophthalmic image.

18. The system of claim 16, wherein:
the neural network is hosted on a server remote from the computing device and accessible via the computer network; and
the computing device instructs the submission of the test ophthalmic image to the neural network on the host server over the computer network.

19. The method of claim 2, wherein diagnosed ophthalmic samples in the diagnostic library are from patients different from the patient associated with the test ophthalmic image.

20. The method of claim 14, wherein the test ophthalmic image is of a first patient and the displayed diagnosed ophthalmic sample is of different patient.

21. The system of claim 16, wherein diagnosed ophthalmic samples in the diagnostic library are from patients different from the patient associated with the test ophthalmic image.

* * * * *

UNITED STATES PATENT AND TRADEMARK OFFICE
CERTIFICATE OF CORRECTION

PATENT NO. : 10,719,932 B2
APPLICATION NO. : 15/909658
DATED : July 21, 2020
INVENTOR(S) : Nathan D. Shemonski et al.

Page 1 of 1

It is certified that error appears in the above-identified patent and that said Letters Patent is hereby corrected as shown below:

In the Claims

In Column 15, Line 28, in Claim 14, after "associated" insert -- with --.

Signed and Sealed this
Twenty-second Day of September, 2020

Andrei Iancu
*Director of the United States Patent and Trademark Office*